United States Patent
Ousdigian et al.

(10) Patent No.: US 6,931,279 B2
(45) Date of Patent: Aug. 16, 2005

(54) METHOD AND APPARATUS FOR IMPLEMENTING TASK-ORIENTED INDUCTION CAPABILITIES IN AN IMPLANTABLE CARDIOVERTER DEFIBRILLATOR AND PROGRAMMER

(75) Inventors: Kevin T. Ousdigian, Shoreview, MN (US); Seema Padmanabhan, Maple Grove, MN (US); James E. Willenbring, St. Paul, MN (US); Paul G. Krause, St. Louis Park, MN (US); James H. Ericksen, North Oaks, MN (US); Paul J. Degroot, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 474 days.

(21) Appl. No.: 10/131,560

(22) Filed: Apr. 22, 2002

(65) Prior Publication Data

US 2003/0199927 A1 Oct. 23, 2003

(51) Int. Cl.⁷ ................................................. A61N 1/39
(52) U.S. Cl. ............................................................. 607/7
(58) Field of Search ........................... 607/4, 5, 14, 30, 607/32, 7, 59

(56) References Cited

U.S. PATENT DOCUMENTS

| 4,556,063 A | 12/1985 | Thompson et al. .... 128/419 PT |
| 4,601,291 A | 7/1986 | Boute et al. |
| 5,127,404 A | 7/1992 | Wyborny et al. ......... 128/419 P |
| 5,129,392 A | 7/1992 | Bardy et al. ............. 128/419 D |
| 5,312,449 A * | 5/1994 | Nigam ......................... 607/14 |
| 5,458,619 A | 10/1995 | Olson ............................ 607/4 |
| 5,709,711 A | 1/1998 | Fain |
| 5,954,753 A | 9/1999 | Alt et al. |
| 6,289,248 B1 * | 9/2001 | Conley et al. ................ 607/59 |
| 6,345,200 B1 | 2/2002 | Mouchawar et al. |

FOREIGN PATENT DOCUMENTS

EP          0 011 946 B2     5/1992    .......... A61N/1/362

OTHER PUBLICATIONS

Swartz et al., "Influence of T–Wave Shock Energy on Ventricular Fibrillation Vulnerability in Humans," Journal of American College of Cardiology, 1995 Conference Abstracts, Feb. 1995.
Karolyi et al., Timing of the T–Wave Shock for Inducing Ventricular Fibrillation in Patients With Implantable Cardioverter Defibrillators, PACE NASPE Abstracts, vol. 18, Apr. 1995 (Part II), p. 802.

* cited by examiner

Primary Examiner—George R. Evanisko
(74) Attorney, Agent, or Firm—Michael C. Soldner; Girma Wolde-Michael

(57) ABSTRACT

The invention provides systems to prevent the delivery of anti-tachycardia pacing (ATP) following a defibrillation threshold (DFT) induction at implant. An algorithm that classifies episodes as induced or spontaneous is implemented, thereby enabling the ATP during charging feature to be operable only when spontaneous episodes are detected while temporarily suspending the ATP feature during the delivery of defibrillation shock after induction has been confirmed. Further, a user interface enables users to interact with an implantable medical device (IMD), particularly for setting a defibrillation threshold (DFT) or a 50 Hz burst from a single programmer screen. The user interface includes various functionalities to promote quick user access to parameters that govern diagnosis, therapy and other features of the IMD. A single screen enables the user to complete automatic and/or manual DFT inductions or a 50 Hz burst from a programmer interface while acquiring associated documentation from the same interface.

6 Claims, 8 Drawing Sheets

FIG. 3C

| | Rx1 | Rx2 | Rx3 | Rx4 | Rx5 | Rx6 |
|---|---|---|---|---|---|---|
| VF Therapy Status | On | On | Off | Off | Off | Off |
| Energy | 8 J | 20 J | | | | |
| Pathway | AX>B | AX>B | | | | |

ATP... Off

ATP + Charging is not Delivered for T-Shock or 50 Hz Inductons — 95

Detection

VF Enable: On
VF Interval (Rate): 320 ms (188 bpm)
VF Initial NID: 18/24
VF Redetect NID: 12/16

Sensitivity
Ventricular: 1.20 mV

Tests – EP S | Adjust Permanent

Inductions/T
- T-Shock
- 50 Hz Burst
- Manual Burs
- PES
- Defibrillation
- Cardioversio
- Ramp Time Since Last Induction (mm): 00:00

< Params  < Tests  < Reports  < Patient  < Session

90

METHOD AND APPARATUS FOR IMPLEMENTING TASK-ORIENTED INDUCTION CAPABILITIES IN AN IMPLANTABLE CARDIOVERTER DEFIBRILLATOR AND PROGRAMMER

FIELD OF THE INVENTION

This invention relates generally to the treatment of cardiac arrhythmias, and more particularly to a method and apparatus for inducing fibrillation. More particularly, the invention relates to performing all induction steps from one programmer screen without interaction with other tasks that could interfere with defibrillation threshold (DFT) testing.

BACKGROUND OF THE INVENTION

It has long been recognized that cardiac defibrillation can be accomplished through application of an electrical shock to the cardiac muscle. See, for example, Swartz et al., "Influence of T-Wave Shock Energy on Ventricular Fibrillation Vulnerability in Humans," Journal of American College of Cardiology, 1995 Conference Abstracts, February 1995; see also, Karolyi et al., "Timing of the T-Wave Shock for Inducing Ventricular Fibrillation in Patients With Implantable Cardioverter Defibrillators," PACE NASPE Abstracts, Vol. 18, April 1995 (Part II), p. 802.

Numerous types of defibrillating devices, both external and implantable, are available for the purpose of cardiac defibrillation through electrical stimulation. One example of an implantable cardiac defibrillator (ICD) is the Medtronic® Gem® III DR, Model 7275 ICD, commercially available from the Assignee of the present invention.

During the implantation process and subsequent periodic followup sessions, the physician tests the capabilities of the ICD to ensure its ability to provide therapy. One method of testing a defibrillator's capability to reliably defibrillate the heart involves induction of an episode of fibrillation in the patient's heart, and then allowing the ICD to detect and terminate the induced fibrillation. The ICD itself has the capability of inducing fibrillation both during the implantation procedure or, later, during regular follow-ups. A command to start an induction, as well as other associated parameters required for a successful induction and therapy, are downloaded to the ICD via a programmer such as the Medtronic® Model 9790 programmer.

It is known in the art that fibrillation can be induced in either chamber of the heart (atrial or ventricular) by delivering a stimulus during that chamber's repolarization phase. In other words, delivery of electrical stimulus is preferable within a so-called "vulnerability window" following the chamber's depolarization period when the heart has begun to repolarize but has not completely repolarized. This process is disclosed, for example, in U.S. Pat. No. 5,129,392 (the '392 patent) issued to Bardy et al., which is incorporated herein by reference in its entirety.

According to the '392 patent, the pulse intended to induce fibrillation is delivered in a timed relationship to an immediately preceding pacing pulse. An overdrive pacing and capture detection protocol or equivalent is carried out to determine the patient's Q-T interval, enabling a subsequent fibrillation-inducing shock to be delivered at a time known to fall near the end of this interval but prior to the conclusion of the repolarization phase. The method and apparatus, disclosed in the '392 patent, are believed to allow for extremely accurate placement of the fibrillation-inducing shock relative to the refractory period of the patient's heart.

The Medtronic® Gem® III ICD is an example of a commercially available device that is capable of delivering a stimulus during the repolarization phase to induce fibrillation. As is well known in the art, such devices have various programmable features. For example, the Gem III's T-Shock feature requires programming of the following major parameters that include: the rate at which overdrive pacing pulses are delivered to pace at a rate known to be above the patient's intrinsic cardiac rate, the amplitude of fibrillation inducing shocks, and the shock coupling interval relating to the interval from delivery of the last overdrive pacing pulse to the delivery of the fibrillation-inducing shock.

Some clinicians may regard programming several parameters to effect automatic fibrillation induction as inconvenient or undesirable, especially if these parameters require access from several different programmer screens. Although a set of nominal or default parameters can be specified for the device, such nominal parameters may not be appropriate for some patients, such as those on anti-arrhythmic drugs that slow conduction.

In the interest of implant efficacy and time constraints, it is desirable to have the ability to program all the various required induction and defibrillation parameters from a single task-oriented induction screen.

SUMMARY OF THE INVENTION

The present invention enables the user to perform all the major required tasks associated with DFT or a 50 Hz burst from a single programmer screen. The single screen includes various functionalities. For example, programmer displayable screen provide tools to control access and enable users to change vital detection and therapy parameters from the induction screen; automatic collection of episode data by the ICD including high voltage lead impedances from shock episode duration, programmed and delivered energy, pathway of shocks, charge time, cycle length/rate during episode, type of episode detected, EGMs, and markers for episodes; controls to retrieve, display, and print vital parameters and episode information from the induction or a 50 Hz burst screen; and an automatic timer that monitors time between inductions and allows the user to reset this timer.

Alternate embodiments may have other easily accessible parameters including, without limitation, the following: temporary sensing, detection, and therapy parameters that apply only during inductions or a 50 Hz burst; automatic downloading of data from the ICD to the programmer after data has been collected; programmer-generated summary of all inductions; user-initiation of separate manual inductions; automatic storage of the EGM related to the induction generated episode or a 50 Hz burst in a permanent memory location for retrieval at future follow-ups; real-time view of ECG, EGM, and Marker Channel® annotations; the capability to automatically resume detection following induction or a 50 Hz burst; and an algorithm to classify the episode as either induced or spontaneous which classification will be used for collection and reporting purposes.

Overall, the present invention should make DFT induction or implementation of a 50 Hz burst simpler and faster. Specifically, the present invention allows the user, among others, to program crucial sensing, detection, and therapy options directly from a single induction or a 50 Hz burst screen. The single screen will allow the user to complete automatic and/or manual DFT inductions or a 50 Hz burst from a programmer interface while acquiring associated documentation from the same interface. The use of a single interface will replace the present need to "hop" to various screen locations to perform these tasks. The present invention also increases patient safety, in that the user is able to program temporary DFT test values. The use of permanent settings may lead to inadvertent errors in therapy delivery.

The present invention also simplifies post-induction data analysis by providing users various tools and interactive displays to cross-reference and incorporate data for better analysis, monitoring and delivery of cardiac therapy.

Furthermore, the present invention includes an embodiment to temporarily disable the antitachycardia pacing (ATP) during charging feature, to prevent the delivery of ATP following a DFT induction at implant. Under current practice, the ICD would need to be shipped from the factory with ATP during charging "off." The present invention uses an algorithm that classifies episodes as "induced" or "spontaneous." Thus, the ICD may be shipped with ATP enabled to perform ATP during charging only when spontaneous episodes are detected. Further, the ICD will deliver a defibrillation shock only during induced episodes that are used to test and determine the shock's effectiveness while maintaining ATP temporarily suspended.

BRIEF DESCRIPTION OF THE DRAWINGS

FIGS. 3b and 3c illustrate how the programmer screen in FIG. 3a might be equipped to enable the user to select when or if ATP during charging will be delivered.

DETAILED DESCRIPTION OF THE DRAWINGS

Figure 1:
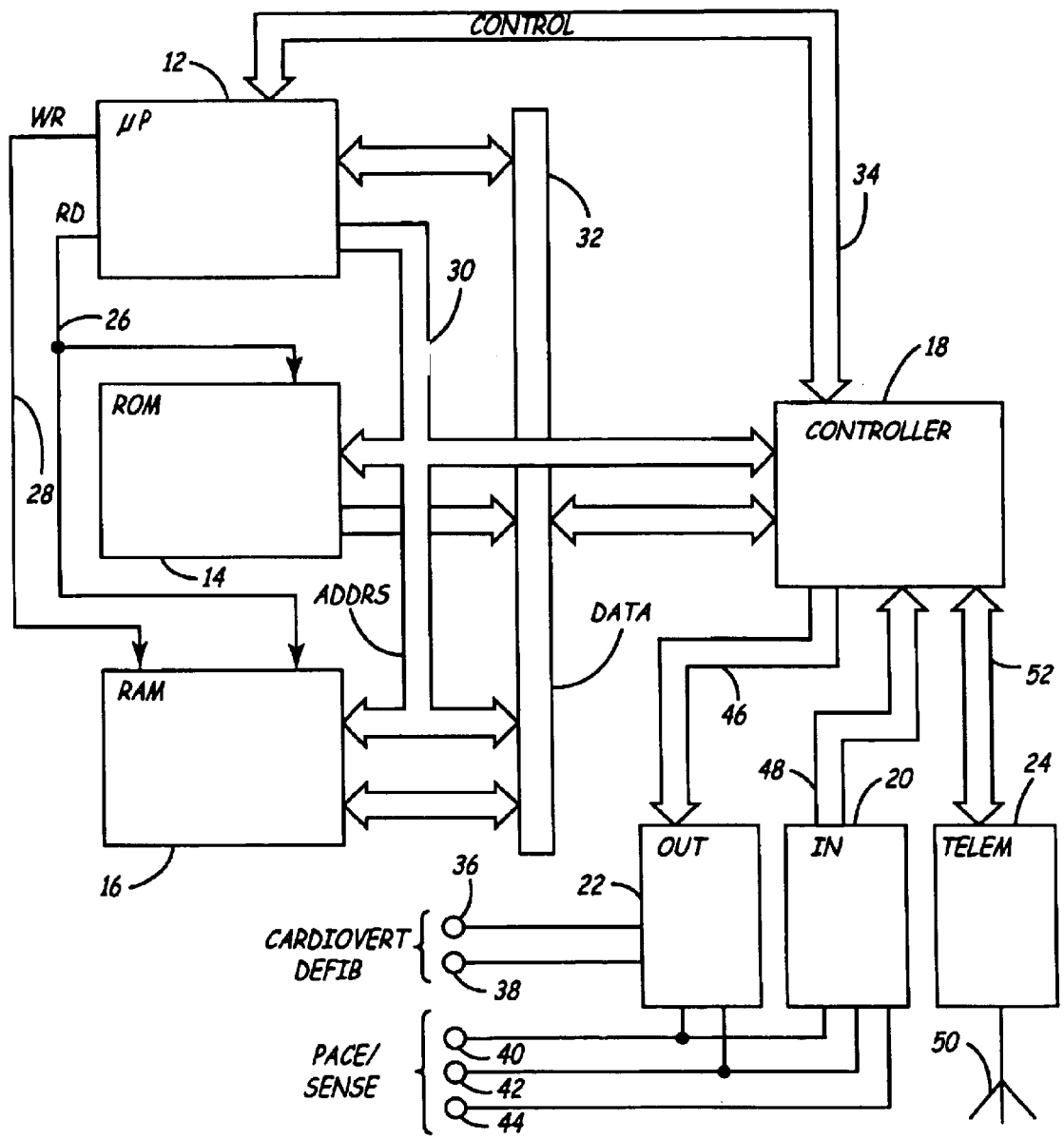
FIG. 1 is a functional block diagram of an implantable cardioversion and defibrillation system with which the present invention may be practiced.

FIG. 1 is a functional block diagram of an ICD system 10 of a type with which the present invention may be practiced. Although the invention shall be described herein in connection with the microprocessor-controlled system 10 of FIG. 1, it is understood that the present invention may be practiced in connection with many different types of systems for the treatment of cardiac disorders, including systems which incorporate a custom integrated circuit controller, or with devices that utilize analog timing and control circuitry. As such, system 10 of FIG. 1 should be considered merely exemplary, rather than limiting, with regard to the scope of applications of the invention.

The primary components of system 10 as shown in FIG. 1 are a microprocessor 12, read-only memory (ROM) 14, random-access memory (RAM) 16, a digital controller circuit 18, input and output amplifiers 20 and 22, respectively, and a telemetry circuit 24. As is well known in the art, the various components of device 10 are powered with an internal power supply, typically a low-voltage, high-current lithium-silver-vanadium battery or equivalent is implemented.

In accordance with common practice in the art, ROM 14 stores basic programming for the device, including instructions defining the computations to be performed by the device to derive the various timing intervals needed for the device to operate in accordance with a predetermined operational algorithm. RAM 16, on the other hand, may store programming for the device, but also serves to store dynamic values of variable control parameters and the like, such as the programmable pacing rate, programmed cardioversion and defibrillation intervals, pulse widths, pulse amplitudes, and so forth, which are programmed into the device by a physician or clinician. RAM 16 may also store derived values, such as the intervals between detected cardiac events, among others.

RD line 26 controls the reading of data from ROM 14 and RAM 16. WR line 28 controls the writing of data to RAM 16. An address bus 30 and a data bus 32 interconnect ROM 14, RAM 16 and microprocessor 12. In response to assertion of the signal on RD line 26 ("the RD signal"), the contents of ROM 14 or RAM 16 designated by the address information present on address bus 30 upon assertion of the RD signal are driven onto data bus 32. Similarly, in response to assertion of a signal on WR line 28 ("the WR signal"), information on data bus 32 is written into a location in RAM 16 designated by the address information then present on address bus 30.

Controller 18 performs the basic timing and control functions for system 10. Controller 18 preferably includes at least one programming timing counter, initiated, for example, upon sensing of ventricular contractions, paced or sensed. This timing counter may be used to define the various timing intervals that must be defined or measured by system 10 in order to operate in accordance with its pacing, cardioverting, and/or defibrillating operational algorithms. The timing intervals that the timing counter in controller 18 counts are controlled by data stored in ROM 14 or RAM 16.

Controller 18 also triggers output pulses from output stage 22, as will be hereinafter described in further detail, and generates interrupts to microprocessor 12 on a control bus. For example, controller 18 may generate interrupts to microprocessor 12 upon the detection of various cardiac events.

Output stage 22 contains a high-energy pulse generator capable of generating cardioverting and/or defibrillating pulses, as will be hereinafter described in further detail. High-energy output pulses from the pulse generator in output stage 22 are applied to the patient's heart (not shown in FIG. 1) via electrodes 36 and 38, which are typically large surface area electrodes disposed on or in the heart. Any of the known prior art cardioversion/defibrillation electrode systems would be suitable for the purposes of practicing the present invention.

Output stage 22 is further coupled to electrodes 40, 42, and 44 that are employed to accomplish bradycardia pacing of the heart. One of electrodes 40, 42, and 44 is typically disposed on the distal end of a cardiac pacing/sensing lead such that it may be situated, for example, at or near the apex of the ventricle of the heart. Another one of electrodes 40, 42, and 44 is preferably a ring electrode spaced back from the distal end of the cardiac pacing/sensing lead. Still another one of electrodes 40, 42, and 44 is typically a common or indifferent electrode, and in one embodiment the implantable device's hermetic, conductive enclosure functions as this indifferent electrode, in accordance with common practice in the art.

Output stage 22 receives control signals from controller 18 via a control bus 46, such that controller 18 can determine the time, amplitude, and pulse width of pulses to be delivered by output stage 22, and to determine which electrodes will be used for delivery of the pulses.

Sensing of heart activity, both intrinsic and stimulated, is accomplished by input amplifier circuit 20, which is also coupled to electrodes 40, 42, and 44. Electrodes 40, 42, and 44 are preferably employed to detect cardiac activity, e.g., ventricular depolarizations, and may be used to determine whether pacing pulses have captured the heart.

Signals indicating the occurrences of sensed cardiac activity are provided to controller 18 via a bus 48. Controller 18 passes data indicative of the occurrence of various cardiac events to microprocessor 12 via bus 34, in the form of interrupts which serve to prompt microprocessor 12 to perform any necessary calculations and/or update values stored in RAM 16.

External control of implantable system 10 is accomplished via telemetry block 24, which facilitates communication between implantable system 10 and an external programming unit (not shown). Typically, such telemetric communication involves the transmission of radio-frequency signals between implantable system 10 and the external device. Thus, an antenna 50 is typically provided in implantable system 10. Telemetry systems appropriate for the purposes of practicing the present invention are disclosed in U.S. Pat. No. 4,556,063 issued to Thompson, et al., and in U.S. Pat. No. 5,127,404 issued to Wyborny et al. The '063 and '404 patents are each hereby incorporated by reference herein in their respective entireties. An example of a commercially available external programming unit suitable for the purposes of practicing the present invention is the Medtronic Model 2090 Programmer.

Information received by telemetry circuitry 24 is passed to controller 18 via a bus 52. Similarly, information from system 10 is provided to telemetry block 24 via bus 52 for transmission to the external programming unit.

As noted above, the present invention relates to the induction of fibrillation in a patient in order to assess the efficacy of a system such as system 10. In accordance with the present invention, inducing fibrillation may be accomplished through the delivery of any one of a plurality of waveforms delivered from the discharge of a single energy storage device (e.g., capacitor) in output stage 22.

Figure 2:
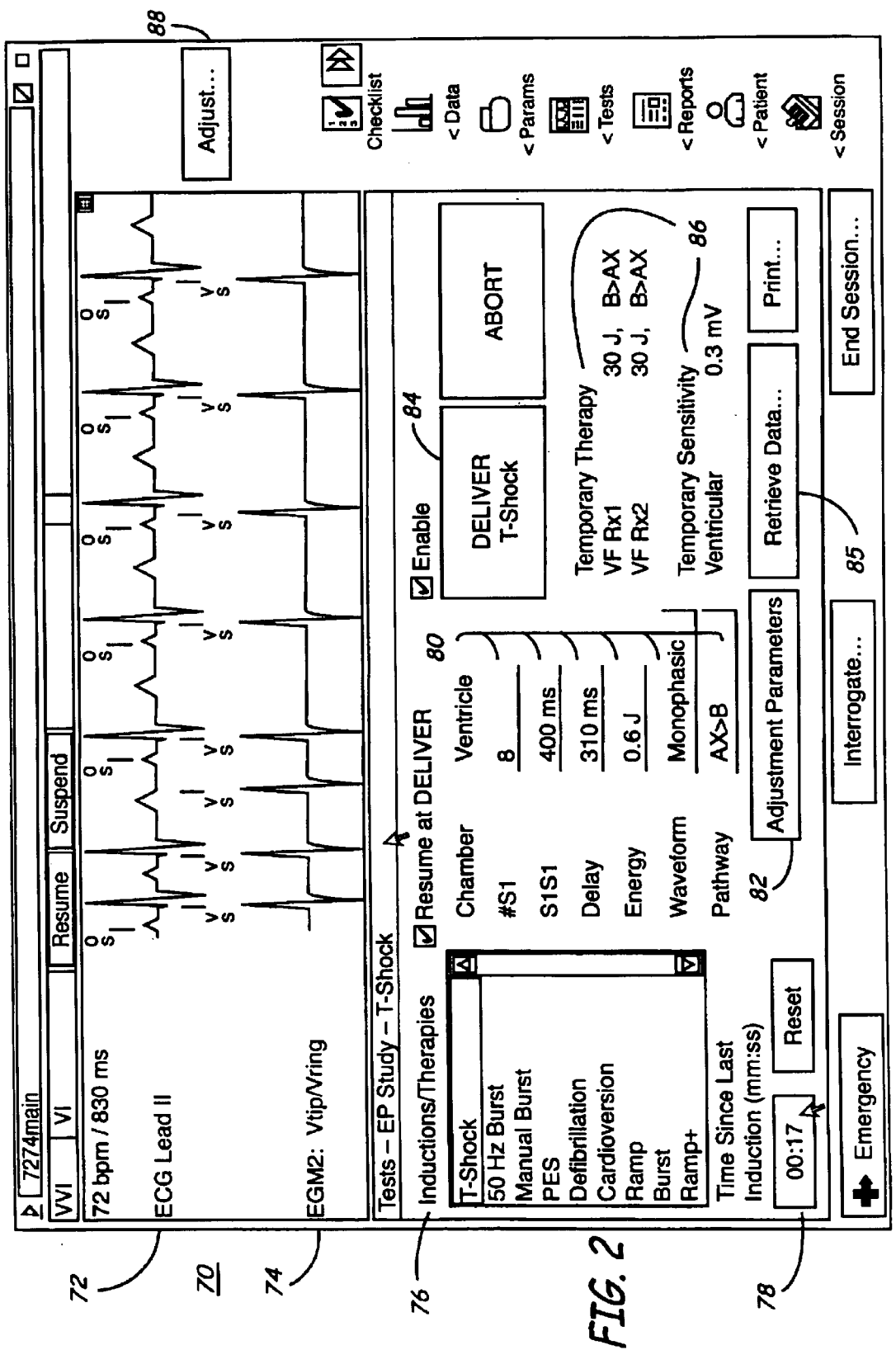
FIG. 2 is an illustration of a prototype programmer screen displaying top-level screen in accordance with the present invention.

In FIG. 2, top-level induction screen 70 illustrates a display of one of a plurality of ECG lead vectors 72 and one of a plurality of EGM pathways 74. As depicted herein, EGM pathways 74 represents ventricular lead tip electrode to ventricular lead ring electrode (Vtip/Vring). Selecting Adjust button 88 opens screen fully to allow selection(s) of other ECG/EGM vectors.

The physician makes use of Inductions/Therapies listed in scroll down menu box 76 for easy selection. For example, DFT inductions use either T-Shock or a 50 Hz Burst to induce ventricular fibrillation. Scroll bar (located at right edge of box 76) allows the physician to scroll through items displayed in box 76 as well as others that may be too numerous to appear as top-level items in box 76. Timer Counter 78 starts its count whenever a T-Shock or 50 Hz Burst is delivered and will continue to run until it reaches 10 minutes or another induction period is started. Timer 78 will count to provide the user with information relating to elapsed time since the initiation of induction. If the duration is greater than 10 minutes, duration of induction will appear as ">10:00." Reset button to the right of timer 78 may be used to restart timer counter 78 either during induction or after a successful termination of the induced VF.

The screen lists settings 80 for defibrillation and easy visualization by the physician. Adjust Parameters button 82 activates a programmer screen (see FIG. 3a) prior to induction. DFT induction is activated by pressing button 84 (in this case, "T-Shock"). Settings 80 remain in effect until the DFT process is terminated, that is, a successful termination of a VF. A short list of temporary programmed settings for therapy and sensitivity 86 reflects the temporary settings programmed on the Adjust Parameters screen (see FIG. 3). Retrieve Data button 85 activates device interrogation and brings up a new screen (see FIG. 4) that displays an episode summary and high voltage therapy data for the most recent episode with a "Quick Link" to more detailed episode information.

Figure 3A:
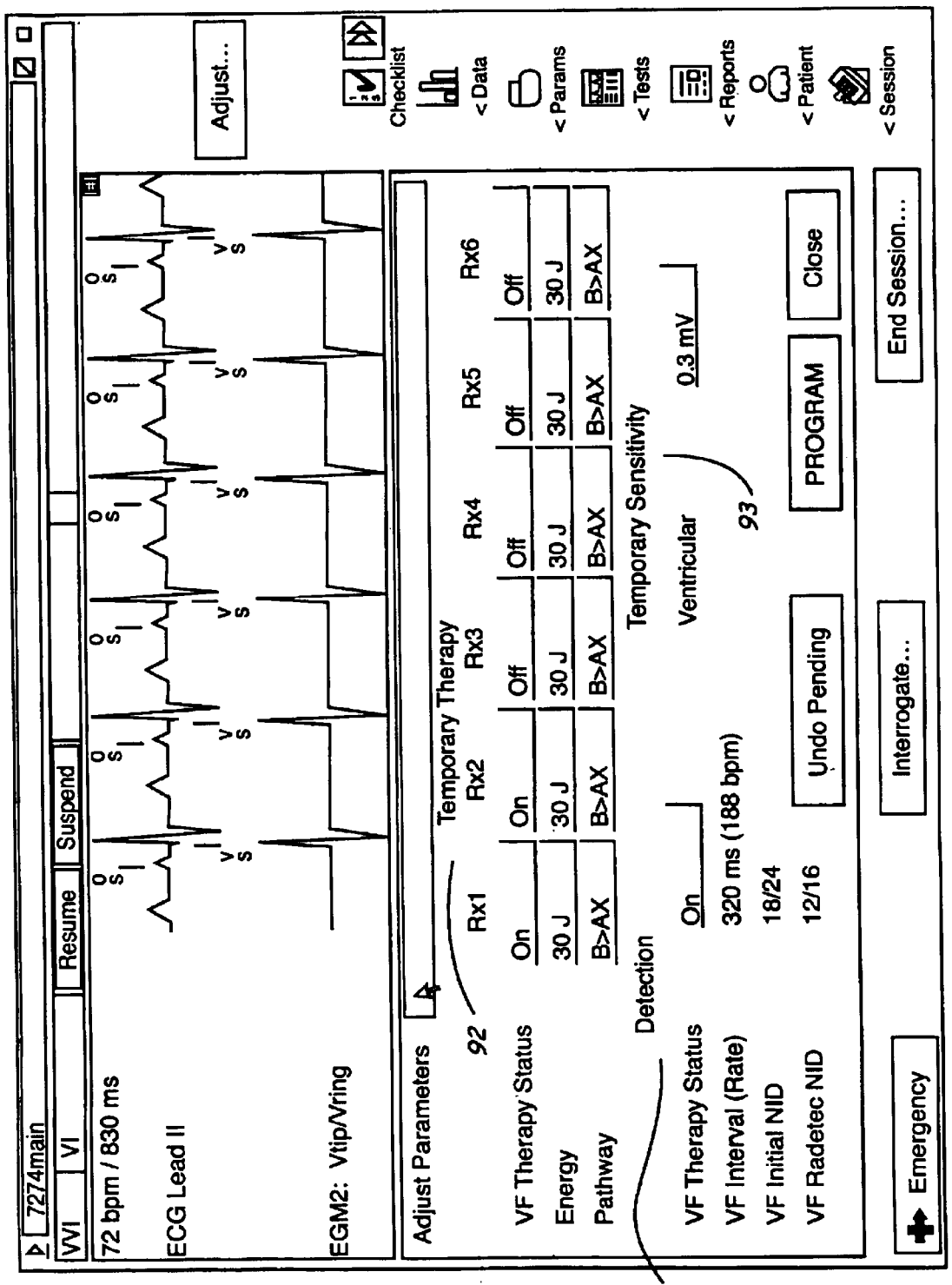
FIG. 3a is an illustration of a programmer screen that is exemplary of a secondary level screen display for use to program settings tailored to induce ventricular fibrillation or other tests and therapies.

Screen display 90 in FIG. 3A may be accessed by pressing Adjust Parameters button 82 (FIG. 2). Screen 90 displays the temporary parameters used to execute an induction, or perform other tests, such as an EP test, among others. Detection 92 of the VF episode allows the physician to turn VF detection on or off. Temporary Therapy 94 has three adjustments, including status (On or OFF), energy (output in Joules), and shock pathway (between implanted electrodes). This feature enables adjustments for up to six therapies. Further, temporary sensitivity 93 may be adjusted to a greater or lesser ventricular sensitivity setting.

Figure 3B:

FIG. 3B represents an alternative embodiment of screen 90. The physician has the option of checking 91, and activating the "Disable ATP during Charging for Inductions" to thereby disable the ATP during charging feature. Without being checked, the system will operate in accordance with the disclosure of FIG. 3B. Message 95 will be displayed if box 91 is checked off.

Figure 4:
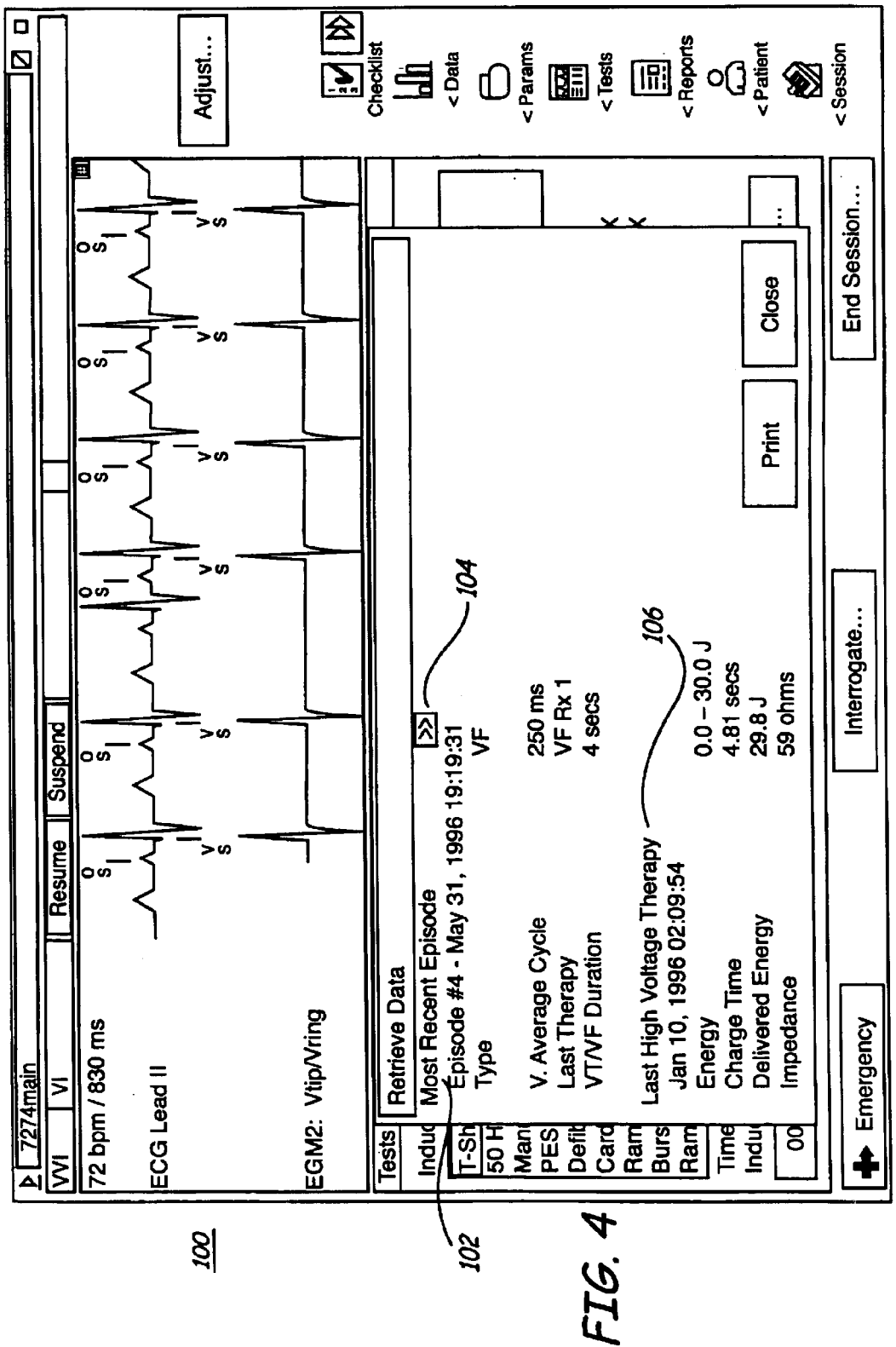
FIG. 4 is a illustration of a programmer screen that is exemplary of a secondary level screen display for use to report data relating to recently induced episodes, previous episode logs, and the last delivered high voltage therapy.

In FIG. 4, retrieve data screen 100 is displayed upon touching retrieve data button 85 (FIG. 2). Data screen 100 displays most recent episode 102 that provides the user with episode number, date and time of day at which the episode occurred, as well as the type of episode. Most recent episode 102 also includes data on: V-cycle length, previous/last therapy, and duration of the episode (in time). The data displayed at the top portion data screen 100 relates to the episode in progress. If the physician wishes to view more detailed information on previous episodes, arrow button 104 is provided to enable access to the log of previous episodes and therapies.

The last high voltage therapy 106 provides date/time stamped information on the last shock therapy relating to information about energy, charge time (for capacitors), delivered energy, and system impedance. This information is valuable to the physician since it is needed for evaluation of device performance, therapy effectiveness, or provides options to alter the parameters relative to the data shown in last high voltage therapy 106.

Figure 5:
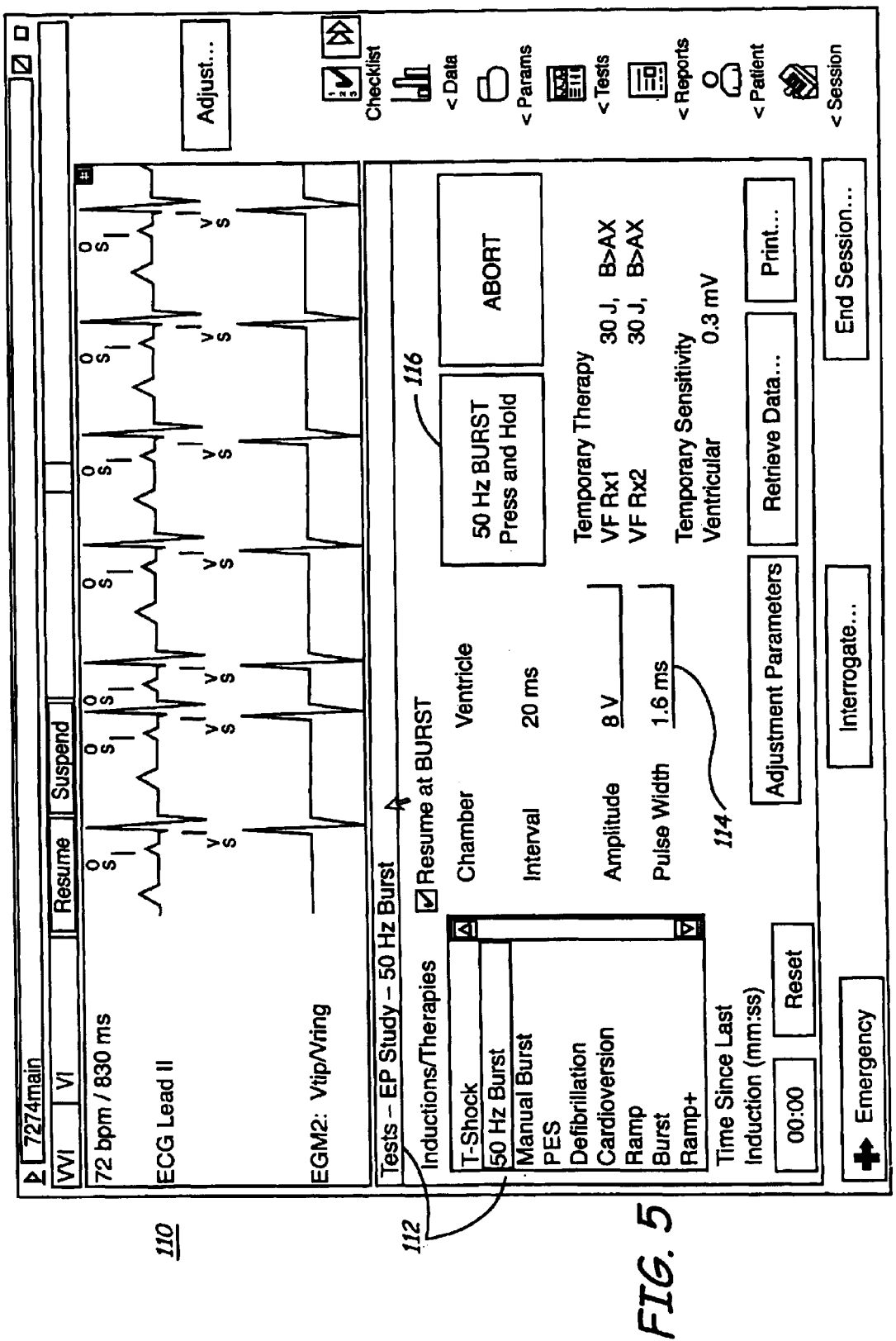
FIG. 5 is a screen display of a prototype programmer screen that is exemplary of a top-level screen that illustrates the screen use for a 50 Hz burst, another embodiment of the present invention.

FIG. 5 is a screen display 110 of the second aspect of the preferred embodiment of the present invention. Specifically, display 110 relates to the delivery of a 50 Hz burst 112 that may, for example, without limitation, induce a ventricular tachycardia, flutter, or fibrillation. The portion of screen 114 informs the physician of the temporary parameters that are in effect during the 50 Hz burst. To activate the burst, the physician selects 50 Hz burst button 116. 50 Hz burst button includes a press and hold function. The remaining buttons serve the same functions as illustrated in FIG. 2.

Figure 6:
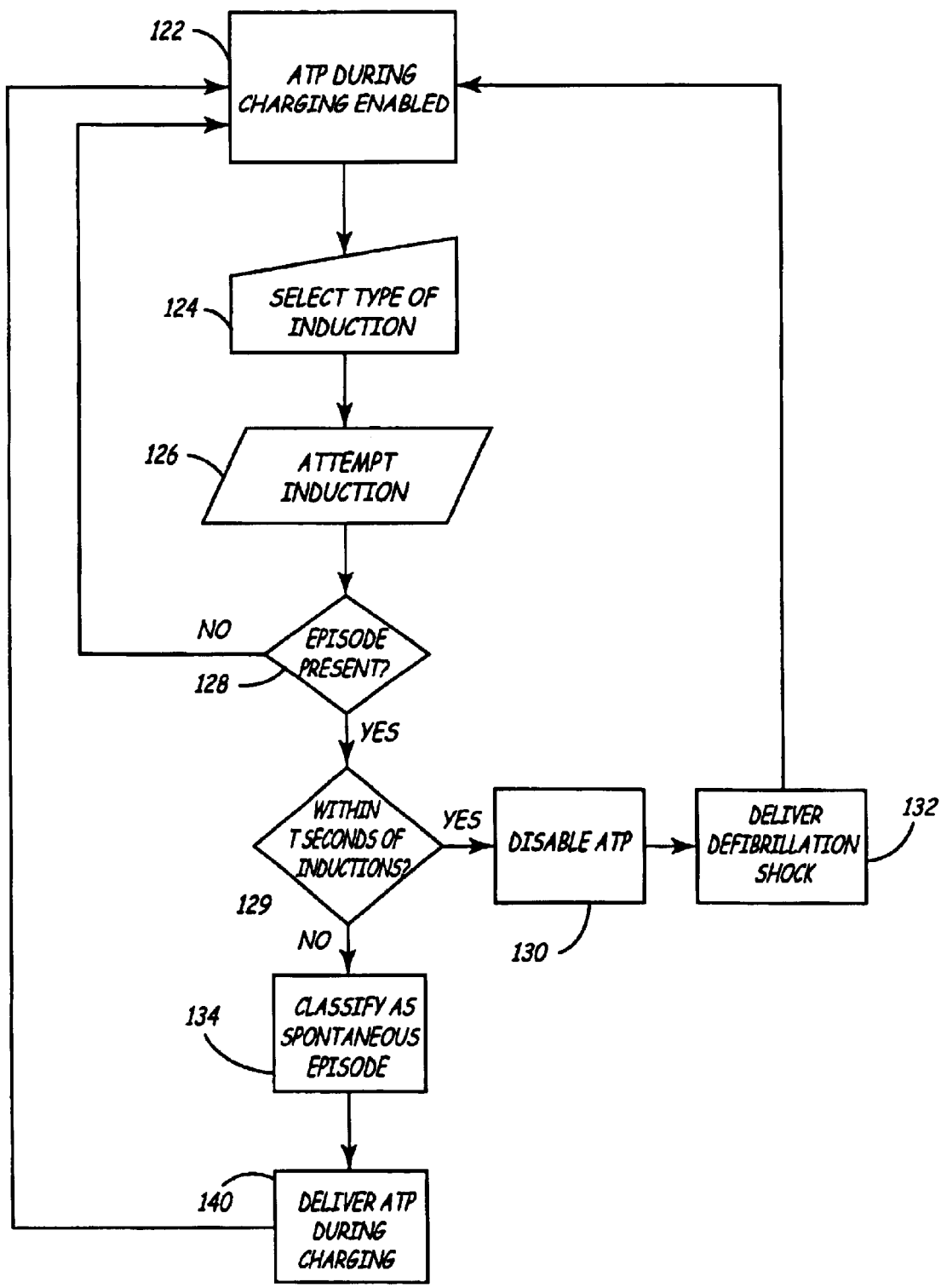
FIG. 6 is a logic flow diagram illustrating algorithmic/software program process implemented in the ICD to determine whether a fibrillation episode is induced or spontaneous and whether to deliver ATP or a defibrillation shock.

FIG. 6 is an illustration of another preferred embodiment of the present invention. ATP is a therapy used during charging of capacitors in an implanted medical device. The general approach of ATP is to terminate a spontaneous ventricular tachycardia without subjecting the patient to a high voltage shock. The general concepts of ATP are disclosed in U.S. Pat. No. 5,458,619 issued to Olson and is incorporated herein by reference in its entirety.

Current medical practice calls for the induction of a fibrillation episode to determine the efficacy of the programmed defibrillation shock in restoring the heart to its normal rhythm. ATP, if enabled, is delivered during capacitor charging, prior to shock delivery. If ATP therapy is successful, the physician will be unable to determine the success or lack thereof of the programmed defibrillation shock. Hence, without the present invention, manufacturers such as Medtronic will need to ship their ICDs with ATP off, so as not to interfere with the required DFT test at implant. After the DFT test at implant, the physician will be expected to enable ATP therapy.

The present invention provides apparatus and method that enables shipment of ICDs with the ATP features activated. Further, one feature of the present invention includes disablement of ATP during capacitor charging by classifying fibrillation episodes as either spontaneous or induced. This feature enables delivery of ATP therapy during charging for terminating spontaneous episodes only.

Referring to FIG. 6, a flow diagram representing high-level software logic implemented to effect the ATP features in accordance with the present invention is shown. At logic step 122, the ICD is shipped with ATP during charging enabled. At step 124, the type of induction is selected by a physician immediately before implant. For example, DFT induction may be selected and induction attempted at logic step 126. This may be executed according to procedures generally outlined in the screen displays of FIGS. 2–5. At decision step 128, the software logic will determine if an episode such as fibrillation is spontaneous or induced. In the event there is no episode present, the logic reverts back to logic step 122. However, if an episode is confirmed, the logic proceeds to decision step 129 wherein the software system checks to see whether the confirmed episode occurred within a duration of t seconds since induction. Any episode that occurs within t seconds will disable the ATP while charging feature under step 130 and subsequently cause a defibrillation shock to be delivered under logic step 132. However, any fibrillation episode that occurs after t seconds is classified as spontaneous episode under step 134 and would trigger an ATP therapy to be delivered under logic step 140. In either case, after the delivery of a shock or delivery of ATP during charging, the system reverts back to logic step 122.

Accordingly, the algorithm of the present invention enables shipping of ICDs with the ATP feature enabled. Further, various user interface features are incorporated to provide ease of use to physicians and other clinical personnel to better manage the delivery of therapy to cardiac patients.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A computer-implemented software system having screen displays to enable user interface with an implantable medical device (IMD), the system comprising:

means for setting ATP during charging feature enabled;

means for selecting at least one type of induction while maintaining said ATP during charging feature enabled;

means for activating induction after selecting said at least one type of induction;

means for confirming the presence of at least one episode subsequent to activating said induction within a set time "t" window;

means for delivering at least one defibrillation shock;

means for classifying episodes as spontaneous subsequent to confirming episodes occurring outside set time window;

means for delivering ATP during charging after confirming episodes as spontaneous; and means for enabling said ATP during charging feature after one of said means for delivering said at least one defibrillation shock and said means for delivering ATP during charging have been triggered.

2. The system of claim 1 wherein the screen displays include interactivity tools, the tools comprising:

means for selecting between ECG and EGM;

means for selecting between inductions and therapies;

means for initializing a timer when a T-shock or 50 Hz burst is delivered;

means for displaying a list of defibrillation settings;

means for displaying a list of temporary parameters;

means for operating VF detection; and means for setting temporary therapy parameters.

3. The system of claim 1 wherein said means for selecting at least one type of induction includes means for programming temporary values.

4. The system of claim 3 wherein said means for programming temporary values further includes programming means for DFT test values.

5. The system of claim 3 wherein said means for programming temporary values includes means for displaying a list of temporary settings for therapy and sensitivity.

6. The system of claim 5 wherein said list of temporary settings includes display tools implemented to execute one of an induction, EP test, functional and operational test.

* * * * *